United States Patent [19]

Line et al.

[11] 4,355,110

[45] * Oct. 19, 1982

[54] PREPARATION OF DEBRANCHING ENZYME FROM RICE FOR PRODUCING A LOW CALORIE BEER

[75] Inventors: William F. Line, Greenfield, Wis.; Vinod K. Chaudhary, Manhattan, Kans.; Etzer Chicoye, Milwaukee; Robert J. Mizerak, Waukesha, both of Wis.

[73] Assignee: Miller Brewing Company, Milwaukee, Wis.

[ * ] Notice: The portion of the term of this patent subsequent to Oct. 19, 1999, has been disclaimed.

[21] Appl. No.: 263,154

[22] Filed: May 13, 1981

Related U.S. Application Data

[63] Continuation-in-part of Ser. No. 141,536, Apr. 18, 1980, abandoned, and Ser. No. 58,823, Jul. 19, 1979, abandoned.

[51] Int. Cl.$^3$ .......................... C12N 9/44; C12C 9/00; C12C 11/04
[52] U.S. Cl. ..................................... 435/210; 426/13; 426/16; 426/29; 435/814; 435/816
[58] Field of Search .................... 426/11, 13, 16, 29; 435/210, 98, 96, 95, 814, 816

[56] References Cited

U.S. PATENT DOCUMENTS

| | | | |
|---|---|---|---|
| 2,692,199 | 10/1954 | Weber | 426/16 |
| 3,379,534 | 4/1968 | Gablinger | 426/13 |
| 3,852,495 | 12/1974 | Schimpf et al. | 426/13 X |
| 3,996,107 | 12/1976 | Martensson | 426/13 X |
| 4,272,552 | 6/1981 | Zastrom | 426/16 X |

OTHER PUBLICATIONS

Willox, et al., The Adddition of Starch Debranching Enzymes to Mashing and Fermentation and Their Influence on Attenuation, MBAA Technical Quarterly, vol. 14, 1977 (pp. 1–25).
Dunn et al., The Limit Dextrinases From Ungerminated Oats and Ungerminated Rice, Carbohydrate Research, vol. 39, 1975 (pp. 283–293).
Dixon et al., Enzymes, Academic Press, Inc., N.Y., 1964 (pp. 13 and 50).
De Clerck; J., A Textbook of Brewing, vol. one, Chapman & Hall Ltd., London, 1957 (pp. 143–147).

Primary Examiner—David M. Naff
Attorney, Agent, or Firm—Quarles & Brady

[57] ABSTRACT

A debranching enzyme (pullulanese) useful in the preparation of a low calorie beer may be obtained from rice by extraction of the rice with an aqueous buffer system having a pH of about 6. A preferred buffer system is 0.1 M potassium phosphate-0.2 M-sodium chloride. Extraction is preferably carried out at a temperature of about 50° C. for about 3 hours. When malted rice is used as the enzyme source a particularly useful mixture of the debranching enzyme and alpha 1,4 carbohydrases is obtained.

3 Claims, 4 Drawing Figures fig. 1 fig. 2 fig. 3 fig. 4

4,355,110

PREPARATION OF DEBRANCHING ENZYME FROM RICE FOR PRODUCING A LOW CALORIE BEER

RELATED CASE

The present application is a continuation-in-part of our earlier copending applications Ser. No. 58,823, filed July 19, 1979 and Ser. No. 141,536, filed Apr. 18, 1980, both now abandoned.

FIELD OF THE INVENTION

The present invention relates generally to a method of preparing a beer. More particularly, it relates to a method of preparing a low calorie beer which comprises introducing enzymes extracted from rice, a traditional brewing source, into the brewing process. It also relates to a method of extracting the enzymes from rice.

DESCRIPTION OF THE PRIOR ART

In the production of beer, yeast is used to ferment into ethyl alcohol a substrate made of a mixture of fermentable carbohydrates. The wort carbohydrates involved which can be fermented by brewer's yeast are normally maltose, glucose, maltotriose and traces of sucrose and fructose. They are obtained by allowing melt enzymes (alpha and beta amylase) to transform starch molecules from malt and other adjuncts into the fermentable sugars outlined above. This is done during the mashing operation. Following mashing the soluble materials are extracted during lautering, leaving behind the spent grain. A clear liquid (wort) is obtained which is transferred to a brew kettle and boiled for a period of time (kettle boil) which inactivates all malt enzymes. Hops are usually added at kettle boil after which the wort is cooled, aerated, pitched with yeast and allowed to ferment. Wort compositions vary depending on the bill of materials, mash cycle employed, etc. However, a typical wort is made up of approximately 65 to 80% fermentable carbohydrates of the type mentioned before and about 20 to 35% nonfermentable carbohydrates. After fermentation a beverage is obtained which usually contains from 3 to 5% alcohol with approximately equal amounts of residual dextrin forming the bulk of dissolved solids, commonly referred to as real extract. This residue remains because of the inability of malt amylases to hydrolyze the alpha 1,6 linkages of the starch. When the wort described below is fermented a product is obtained which contains approximately 110 calories per 12 oz. bottle when packaged at 3.3 g/100 g ethanol.

In the production of low calorie, superattenuated beers, an attempt is made to obtain a higher proportion of alcohol and a much lower amount of residual dextrin. This results in a beer which has a lower specific gravity at end fermentation than normally obtained. The first superattenuated products made were produced by a process which consisted of adding an external enzyme in the fermenter. (See Gablinger U.S. Pat. No. 3,379,534). That particular enzyme, a glucoamylase, has the capability of hydrolyzing both alpha 1,4 and alpha 1,6 linkages of the starch and is usually obtained from the mold *Aspergillus niger*. The use of glucoamylase is not without certain disadvantages. They are the following:

(a) The enzyme has some difficulty hydrolyzing the alpha 1,6 linkages. It is much more efficient at hydrolyzing alpha 1,4 linkages, and, (b) The enzyme may be considered to be exogenous to the brewing process. That is, it is not present nor is it isolated from traditional brewing materials, e.g., malt, rice, corn, or yeast.

Another approach which has been suggested consists of using a bacterial alpha 1,6 carbohydrase or pullulanase isolated from *Aerobacter aerogenes* together with a microbial beta amylase to effect superattenuation. (MBAA Technical Quarterly Vol. 14, p. 105, 1977).

There are three basic classes of starch debranching enzymes. They are the glucoamylases, the isoamylases, and the pullulanases. The distinctions between these classes are well covered in a review article (Lee, E. and Whelan, J. "The Enzymes" 3rd Edition, V, 191, 1971). Basically, pullulanases cleave the alpha 1,6 linkages of pullulan (an alpha 1,6 polymer of maltotriose isolated from a mold cell wall) to yield maltotriose. Pullulanases are specific for alpha 1,6 linkages and can debranch the wort limit dextrins producing alpha 1,4 polysaccharides which can be converted by various alpha 1,4 carbohydrases to sugars which are fermentable by brewer's yeast.

Attempts have been made in the past to isolate a debranching enzyme from sources germane to beer production, such as malt. The so-called "R enzyme" has been reported in the literature. (Lee, E. and Whelan, J., supra). It seems, however, that to date a good efficient way of isolating the "R enzyme" has not been found.

In our earlier application Ser. No. 58,823 filed July 19, 1979, we disclosed our discovery that a low calorie beer could be prepared by a method employing a debranching enzyme extracted from ungerminated whole or polished rice, a traditional brewing material, together with an alpha 1,4 carbohydrase from another source such as an amylase from the variety of grains described below or a fungal glucoamylase.

SUMMARY OF THE PRESENT INVENTION

It is the general object of the present invention to disclose our discovery that rice, a well known traditional brewing material can be used as the source for both a debranching enzyme or a mixture of a debranching enzyme and alpha 1,4 carbohydrases; the mixture is capable of converting the wort limit dextrins to fermentable sugars which the yeast ferments to ethanol to produce a superattenuated beer.

The present invention broadly comprises using rice as the source of a debranching enzyme or a mixture of both the debranching enzyme and the alpha 1,4 carbohydrases in the preparation of a low calorie beer. It also includes a method of isolating the debranching enzyme or a mixture containing both the debranching enzyme and alpha 1,4 carbohydrase from rice.

Rice has traditionally been used in the brewing industry. Usually it is used as an adjunct, or an additional source of carbohydrates, like corn grits or corn syrup. The rice used for this purpose is usually a food grade rice, that is rice which has been put through the conventional drying process and subsequently dry milled. Brewers generally use the broken kernels from the polishing operation. The traditional process consists of using rice in the cereal cooker. Usually some malt is added, together with enough water so that some conversion of rice starch is obtained in the cooker. This mixture is cooked for a period of time and added to the mash where melt enzymes convert the starch from the malt and the rice into fermentable carbohydrates. The rice adjunct used in this fashion has no enzyme activity, all of it having been inactivated in the cereal cooker. The traditional process, therefore, does not use rice as a source of enzyme.

We have discovered that the use of a debranching enzyme which naturally occurs in rice provides good results when used with an alpha 1,4 carbohydrase in the brewing process to prepare a low calorie beer.

We also have discovered that an enzyme mixture obtained from malted or germinated rice is highly effective in reducing branched high molecular weight dextrins to fermentable sugars without the need for addition of alpha 1,4 carbohydrases from another source.

The method of the present invention is an improvement in the method of producing a low calorie or superattenuated beer by fermenting brewers wort with yeast which comprises adding to the wort a debranching enzyme or pullulanase in an amount effective to reduce the amount of residual dextrins in the real extract by cleaving the alpha 1,6 linkages of limit dextrins to form alpha 1,4 dextrins which are converted by 1,4 carbohydrases to fermentable sugars which are fermented by the yeast to alcohol. The enzyme can be introduced at various stages.

In one embodiment, either whole polished rice or the debranching enzyme extracted from polished rice is added to the wort which contains grain amylase from a suitable source (e.g. malt) at the fermentor. The debranching enzyme from the rice hydrolyzes the residual 1,6 linkages of the limit dextrins and the grain amylase cleaves the resulting linear alpha 1,4 polysaccharides into fermentable sugars which are then converted to ethanol by the yeast.

In another embodiment of the method, the debranching enzyme extracted from the whole polished rice is added to the mash to help cleave the 1,6 linkages of the limit dextrins. The natural malt enzymes hydrolyze the 1,4 linkages thus producing higher levels of fermentable sugars.

In still another embodiment, a mixture of enzymes consisting of both a debranching enzyme or pullulanase and alpha 1,4 carbohydrases is obtained from malted or germinated rice. When the mixture of enzymes is used no additional alpha 1,4 carbohydrase is required.

Beer of palatable quality can be produced by each of the above-described procedures. In each instance, the end product has been found to contain a greater proportion of alcohol to real extract and fewer calories per unit of volume when packaged at constant alcohol than a control beer produced with no enzyme addition.

The enzyme which has been found to be useful in the preparation of a superattenuated low calorie beer is a starch debranching enzyme which naturally occurs in rice. The enzyme of the present invention is classed as a pullulanase because it hydrolyzes the alpha 1,6 linkages of the diagnostic substrate pullulan.

The literature contains numerous reports of limit dextrinases which have been derived from a wide variety of grains including barley, rye, corn, wheat, oats, and commercial malts. Messrs. Graham Dunn and David J. Manners, in *Carbohydrate Research*, 39 (1975) 283–293 reported that ungerminated oats and ungerminated rice contain limit dextrinases which will cleave the 1,6 linkages of pullulan.

DETAILED DESCRIPTION OF THE INVENTION

In one extraction method of the present invention the debranching enzyme is extracted from whole or commercially polished rice with an aqueous buffer system having a pH of about 6 at temperatures ranging from 0°–60° C. The preferred conditions are to slurry polished rice in 0.1 M potassium phosphate buffer—0.2 M NaCl, pH 6.0 at about 50° C. for about 3 hr.

The pullulanase-containing supernatant from the extraction may be further purified by a procedure consisting of: (1) acidifying the crude extract and (2) precipitating the rice enzyme with $(NH_4)_2SO_4$. This procedure will be illustrated in the examples below.

The enzyme may be stored in a liquid form, or as a freeze-dried or spray dried powder. The freeze dried powder is obtained by diafiltering the enzyme containing buffered pH 6 extract against 0.1 M ammonium bicarbonate solution. Ammonium bicarbonate is a volatile salt which sublimes on freeze drying to yield a salt free enzyme powder. Other sublimable salts which do not interfere with the process or adversely affect the enzymatic activity also may be used if desired.

The amount of polished or ungerminated rice or extracted enzyme to be added in the brewing process depends on many factors such as the enzymatic content of the rice, the activity of the enzyme, the stage of the brewing process at which it is added and the brewing conditions, e.g., pH, temperature, and time. Generally, the amount of rice or extract to be added will be an amount effective to reduce the amount of residual limit dextrins in the real extract by about 30 to about 80%. Normally, for preconversion of the dextrins prior to fermentation, an enzyme source, either extract or rice, containing from about 100 units to about 300 units of pullulanase activity per liter will be added to the wort or about 300 units to about 700 units per liter to the mash. Smaller amounts containing about 2 units to about 75 units of pullulanase activity per liter are effective when added to the wort in the fermenter. Larger amounts than those normally used can be used if desired or needed. Obviously, some testing may be required to determine the precise amounts to be used. However, such testing and determination are well within the skill of those skilled in brewing art.

In one embodiment of the method, the debranching enzyme is added to the fermentor with a 1,4 carbohydrase, such as a grain diastase. This combination is required because the rice debranching enzyme cleaves the highly branched alpha 1,6 limit dextrins, and the added carbohydrase cleaves the resulting alpha 1,4 dextrins into sugars that can be used by the yeast. The effective amounts of each enzyme to be added will depend upon the content of limit dextrins normally present in the product of the fermentation and the extent of caloric reduction desired. Normally, the debranching enzyme will be present in an amount of at least about 2 units and preferably about 2 units to about 60 units of pullulanase activity per liter of wort and the carbohydrase or grain diastase will be present in an amount ranging from at least about 20 units and preferably about 20 units to about 200 units of amylase activity per liter of wort. Larger amounts of both enzymes may be used but provide no particular advantage.

In still another embodiment, the addition of the rice debranching enzyme to the fermentor is accompanied by the addition of a glucoamylase such as that derived from *Aspergillus niger* which is active vs. both alpha 1,6 and alpha 1,4 linkages. Supplementing the glucoamylase with rice pullulanase at the fermentation stage significantly reduces the fermentation time normally required to prepare a superattenuated beer. Although both of the enzymes possess debranching activity, the rice enzyme is more potent than glucoamylase and as a result the fermentation time is reduced. The concentration of the rice enzyme in such a mixture may be lower than that normally employed, e.g., 2-4 units of pullulanase and the glucoamylase will be present in at least about 2 units and preferably about 2 units to about 10 units of glucoamylase activity per liter.

In a further embodiment, the mixture of debranching enzyme and alpha 1,4 carbohydrases obtained from malted rice is added to wort in the fermentor. The mixture is added in an amount which provides at least about 2 units of the debranching enzyme and preferably about 2 units to 60 units with 15 units especially preferred and at least about 20 units of the alpha 1,4 carbohydrases and preferably about 20 to 200 units with about 100 to 140 units especially preferred.

The following analytical procedures were used in the examples described below. Protein was determined by the Lowry method as modified by Miller (1). Pullulanase activity was determined by hydrolysis of 0.5% w/v pullulan at pH 5.0 and 50° C. Amylase activity was determined by the hydrolysis of 0.5% w/v Linter soluble starch at pH 5.0 and 50° C. The appearance of reducing sugars was monitored by the dinitrosalicylic acid method of Bernfield (2). A unit of activity in both assays was defined as the appearance of 1 mg reducing sugar (as maltose)/minute. Specific activities are expressed as units/mg protein.

Glucoamylase activity was determined by a modification of the method of Pazur (3), using maltose as substrate, at pH 5.0 and 25° C. The appearance of glucose was monitored using the coupled glucose oxidase-peroxidase reaction with o-dianisidine as the indicator dye (3). A unit of activity was defined as the hydrolysis of 1 micromole maltose/minute under these conditions.

Fermentations were monitored by the decrease in specific gravity using the Mettler DMA-45 calculating densitometer. When the beers were judged to be end-fermented, refractive indices were obtained on a Zeiss immersion refractometer. These measurements were used to calculate the alcohol (4,5,6) and real extract (5,6) of the beers. The caloric content of a standard 12 oz. container was calculated at 3.3 g/100 g ethanol, as described by Helbert (7).

Carbohydrate profiles were obtained by high-pressure liquid chromatography on Bio Rad Q 15S resin as described by the ASBC Subcommittee on brewery sugars and syrups (8) and by Scobell, et al (9). Unless otherwise stated, all diafiltrations were performed on an Amicon DC-2 apparatus equipped with an H-1P-10 cartridge (m.w. cutoff=10,000) (Amicon Corporation, Lexington, Mass.).

EXAMPLES

Examples 1-6 will illustrate the isolation and some properties of rice pullulanase.

EXAMPLE 1

Isolation of pullulanase from whole rice

Five-hundred grams seed grade LaBelle rice were blended in 0.1 M potassium phosphate buffer—0.2 M NaCl, pH 6.0, using a Waring blender. The blended grain was transferred to a vessel in a bath maintained at 50° C. and stirred under 2 liters buffer for 3 hr. The spent grain was removed by filtration through cheesecloth and the filtrate clarified by centrifugation.

Further clarification may be achieved by reducing the pH of the extract to 5.0. The resulting precipitate was removed by centrifugation, and the pH of the supernatant was readjusted to 6.0.

The extract may be purified and concentrated by (NH$_4$)$_2$SO$_4$ fractionation. This salt was added to the pH adjusted supernatant at the rate of 40 g solid (NH$_4$)$_2$SO$_4$ per 100 ml solution. The suspension was stirred for 1 hr. at room temperature, and the precipitate was removed by centrifugation. The precipitate was dissolved in and diafiltered vs. the extraction buffer. Table 1 summarizes the extraction of whole rice detailed above.

EXAMPLE 2

Localization of pullulanase within the rice kernel

LaBelle rice from Example 1 was pearled and the following fractions isolated: (1) husks; (2) brown or dehusked rice; (3) rice bran; and (4) polished white rice. Each fraction was extracted and clarified as described in Example 1 for whole rice. Analysis of these extracts, summarized in Table 2 revealed that the great majority of pullulanase activity was localized in the endosperm (polished rice). In addition, this preparation had a much greater specific activity than preparations obtained from either whole or brown rice. Thus, polished rice is the preferred enzyme source.

EXAMPLE 3

Extraction of pullulanase from polished rice

Two kilograms of commercially polished rice were ground to 0.02 inch in a barley mill. The ground rice was doughed into 4 liters of pH 6 extraction buffer, and the suspension was stirred for 3 hours at 50° C.

The pH of the extract was adjusted to 5.0, and the resulting supernatant was clarified by centrifugation. The pH of the supernatant was readjusted to 6.0.

For long-term storage, it was desirable to obtain the preparation as a salt-free powder. This was accomplished by diafiltering the supernatant from the pH adjustment step vs. 0.1 M NH$_4$HCO$_3$. This salt was chosen since: (1) the preparation requires salt to remain in solution; and (2) NH$_4$HCO$_3$ sublimes and is removed by subsequent freeze drying.

Figure 1:
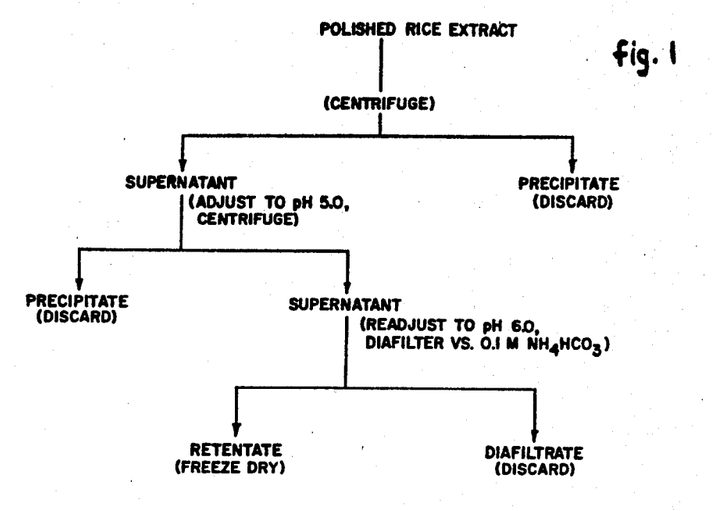
FIG. 1 is a flow chart of pullulanase extraction from polished rice.

After diafiltration vs. 4 volumes of 0.1 M NH$_4$HCO$_3$, the retentate was freeze dried. The results of this extraction are summarized in Table 3 and a flow chart of the extraction is shown in FIG. 1.

EXAMPLE 4

Extraction of rice pullulanase and diastase from malted rice

Seed grade LaBelle rice was steeped in water at 22° C. for 72 hours and then germinated for 5 days at the same temperature. It was kilned at 50° C. Prior to extraction of the enzyme(s), the malted rice was floured in a hammermill so that it passed through a 0.125" screen. The resulting flour was defatted with n-hexane (4 hours, room temperature) to remove lipid. The flour was harvested by filtration and air dried.

The enzymes were extracted from defatted floured malted rice as described for polished rice in Example 3. One hundred grams defatted rice flour were doughed into 200 ml of pH 6 extraction buffer, and the suspension was stirred for 3 hours at 50° C. The spent grain was removed by filtration through cheesecloth and the filtrate was clarified by centrifugation.

Table 13 lists the enzymatic properties of the malted rice extract together with an identical extract prepared from ungerminated polished rice. As is evident from the table: (1) the yield of pullulanase is the same for both preparations, and (2) the amylase yield is increased about 16 fold in the malted rice over the ungerminated polished rice. Note that the pullulanase specific activity of the malted rice extract was about half that obtained with polished rice. However, the protein yield for the malted rice was about twice that obtained from the polished rice extract, i.e. structural protein was extracted from the hull and bran of malted rice which were removed in milling polished rice.

EXAMPLE 5

Effect of pH on rice pullulanase activity

Figure 2:
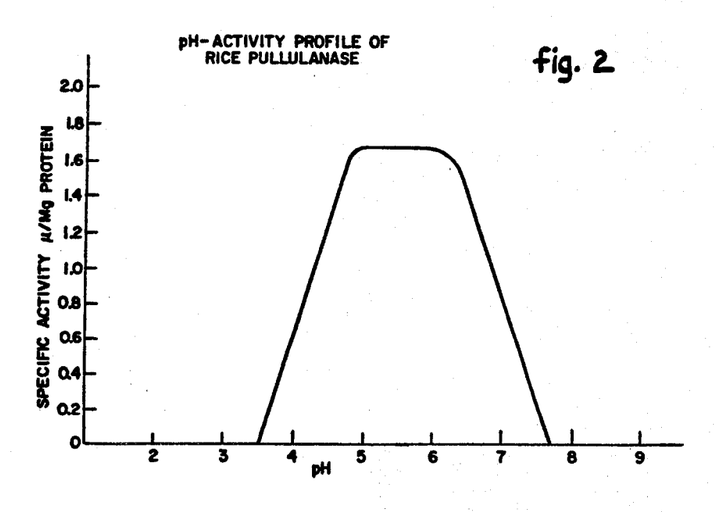
FIG. 2 shows the pH-activity profile of rice pullulanase.

The optimum pH range was determined on rice pullulanase isolated by the procedure outlined in Example 3. The following buffer systems were used: (1) pH 4.0–5.5—0.1 M acetic acid adjusted to the appropriate pH with NaOH; (2) pH 6.0 to 7.0 0.1 M $KH_2PO_4$ adjusted to the appropriate pH with NaOH. Stock pullulan (10% w/v in $H_2O$) was diluted to 1% w/v in the appropriate buffer. Rice pullulanase was then assayed over the pH range 4–7 under standard conditions. The results summarized in FIG. 2 show that optimal activity is obtained in the pH range of 5–6.5.

EXAMPLE 6

Figure 3:
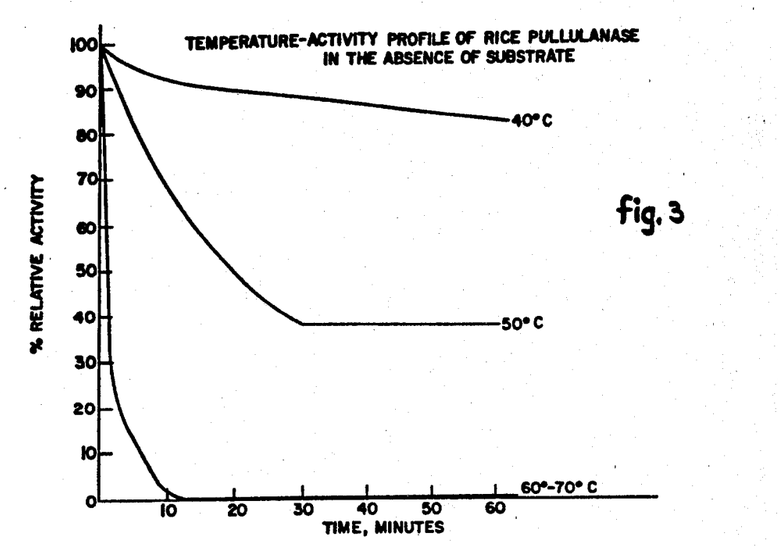
FIG. 3 shows the temperature-activity profile of rice pullulanase in the absence of substrate.

Effect of Temperature on rice pullulanase activity (A) In the absence of substrate Rice pullulanase prepared as described in Example 3 was made to a final concentration of 2 mg/ml in 0.1 M acetate buffer, pH 5.0. Aliquots of this mixture were incubated in the temperature range 40°–70° C. for times ranging from 10–60 min. Aliquots of the incubates were withdrawn, cooled, and subjected to the standard pullulanase assay. The results illustrated in FIG. 3 show that the enzyme was rapidly inactivated at temperatures in excess of 40° C. Complete inactivation occurred at 60° C. after 10 min.

(B) In the presence of substrate

Rice pullulanase prepared as described in Example 3 was made to a concentration of 1 mg/ml in 0.1 M acetate pH 5.0. Aliquots of this preparation (sufficient to yield a final concentration of 0.2 mg/ml incubate) were delivered into tubes containing pullulan and 0.1 M acetate buffer, pH 5.0 which had been equilibrated to the desired temperature. At each temperature (ranging from 40° C.–70° C.), 1-ml aliquots were withdrawn after 10, 20, and 30 minute incubations and inactivated by delivering them into the dinitrosalicylic acid solution used for color development. The reducing sugars were determined in the standard manner.

Figure 4:
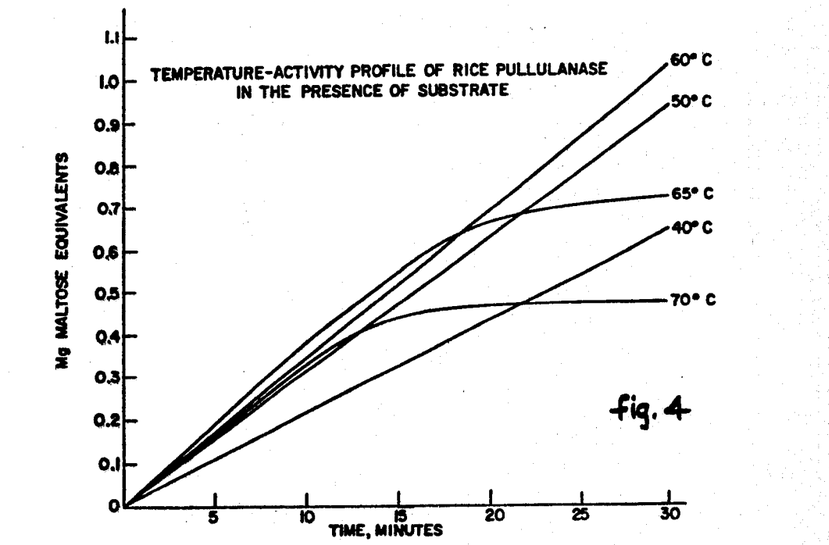
FIG. 4 shows the temperature-activity profile of rice pullulanase in the presence of substrate.

The results of these experiments are illustrated in FIG. 4. It is obvious that the enzyme is stable in the presence of substrate up to 60° C. for 30 min. This is in marked contrast to the temperature stability of the enzyme alone as described in Example 6-A.

Examples 7–15 will illustrate the application of rice debranching enzyme (pullulanase) to the brewing process. Examples 8–12 will illustrate the use of the enzyme in combination with various alpha 1,4 carbohydrases with fermenting beer, while Examples 15 and 17 will illustrate its use prior to fermentation. In all cases, the wort used was mashed as an all-malt wort and was adjusted to about 12° to about 15° P with a commercial syrup prepared from corn starch, prior to fermentation. In the examples which follow the original gravity was constant. The worts were pitched with a stock brewing culture of S. uvarum to a final concentration of $1 \times 10^7$ cells/ml and fermented at 15° C.

EXAMPLE 7

Preparation of grain diastases for use with rice pullulanase (A) Malt diastase

High-gib distiller's malt was ground in a Wiley mill. The powder (250 g) was doughed into 1.5 liters 0.1 M acetate buffer, pH 5.0. The slurry was stirred for 2 hr. at 50° C. and the supernatant was recovered as described for rice crude extract (Example 1).

The enzyme was further purified by adding $(NH_4)_2SO_4$ to a final concentration of 40 g/100 ml. The precipitate was harvested by centrifugation and resuspended in 0.1 M acetate buffer pH 5.0. The suspension was clarified by diafiltration vs. the same buffer, concentrated and stored at 4° C.

(B) Preparation of malt beta-amylase

Malt diastase prepared as in Example 7(A) contains both alpha- and beta-amylase, with alpha-amylase in greatest concentration. Malt alpha-amylase can be selectively inactivated at acid pH (9). The pH of a portion of the malt diastase, prepared as described in Example 7(A), was adjusted to 3.6 and incubated at 35° C. for 2 hr. The solution was clarified by centrifugation, and the pH of the supernatant was readjusted to 5.0.

(C) Preparation of soybean diastase

Whole soybeans were ground in a Wiley mill. Ten gm of powder were stirred in 100 ml 0.01 M acetate buffer, pH 5.2 at 55° C. for 1 hr. The solution was clarified by centrifugation followed by filtration using a filter aid. The filtrate was diluted 4-fold, diafiltered vs. $H_2O$, and concentrated to the original volume. The concentrate was stored at 4° C.

(D) Isolation of wheat diastase

Wheat diastase was isolated from pearled hard winter wheat ground as described in Example 3 for polished rice pullulanase. The powder (50 g) was doughed into 100 ml 0.1 M phosphate buffer—0.2 M NaCl, pH 6.0, and the suspension was stirred for 3 hr at 50° C. The suspension was clarified as described in Example 1 for the rice enzyme.

The supernatant was dialyzed vs. 0.02 M phosphate buffer—0.2 M NaCl Ph 7.0 and then water.

(E) Isolation of barley diastase

Ungerminated barley was ground, extracted and clarified as described for malt diastase in example 7(A). After extraction the supernatant was diafiltered vs. 0.1 M acetate, pH 5.0 and concentrated 3-4 fold prior to use.

The amylase extracted from ungerminated barley is predominantly a beta amylase. Thus the barley diastase described in this example is equivalent to malt beta amylase described in Example 7(B).

Table 4 summarizes the amylase activity of the grain amylases described in Example 7.

The glucoamylase used in the experiments described below was Novo 150 obtained from Novo Industries, Wilton, Conn.

EXAMPLE 8

Superattenuation of fermenting beer using rice pullulanase-malt diastase

The wort formulated as described above was fermented: (1) with no enzyme addition (Beer #1) to establish the attenuation limit; (2) with the addition of glucoamylase (8.1 U/l Beer #2) to establish the superattenuation limit; and (3) with the addition of rice pullulanase (15.3 U/l) and malt diastase (140 U/l Beer #3). In all cases, the worts were pitched and aerated as described above after which the appropriate enzymes were added. The beers were fermented at 15° C. Table 5 lists the enzymes addition rate to the pitched aerated wort.

Table 6 lists the properties of the end-fermented beers described above. The enzyme-free control contained 0.5-0.6 g/100 less alcohol than did either Beer #2 or #3 which were superattenuated with glucoamylase and rice pullulanase/malt diastase, respectively. When packaged at 3.3% ethanol the real extract in Beer #3 was reduced by about 1.0 g/100 g over that in Beer #1 and was nearly identical to that obtained when glucoamylase was used (Beer #2). At this alcohol concentration Beers #2 and #3 would contain 92—93 cal/12 oz as opposed to 108 cal/12 oz for Beer #1.

The carbohydrate profiles summarized in Table 7 show that Beers #2 and #3 had nearly identical carbohydrate compositions at end-fermentation and that in both Beers #2 and #3 the nonfermentable sugars (greater than DP-3) were substantially reduced over that obtained in Beer #1.

EXAMPLE 9

Superattenuation of fermenting beer using rice pullulanase-soybean diastase

The wort was aerated and pitched as in Example 8. Rice pullulanase (15.3 U/l) and soybean diastase (140 U/l) were added according to the schedule listed in Table 5. The beer was fermented as described in Example 8.

The end-fermented beer containing 15.3 U/l of the rice pullulanase and 140 U/l of soybean diastase (Beer #4, Table 6) superattenuated to about the same degree as the glucoamylase control (Beer #2), yielding a beer of 93.4 cal/12 oz when packaged at 3.3 g/100 g ethanol. The carbohydrate profile is given in Table 7 (after 12 days of fermentation) and shows that the nonfermentable fraction was nearly identical to that of the glucoamylase control (Beer #2).

EXAMPLE 10

Superattenuation of fermenting beer using rice pullulanase-wheat diastase

The wort was aerated and pitched as described in Example 8. Rice pullulanase (15.3 U/l) and wheat diastase (140 U/l) were added as shown in Table 5. The beer was fermented at 15° C. as described in Example 8.

Reference to Table 6 shows that this beer (Beer #5) superattenuated to the same level as the glucoamylase control (Beer #2). When packaged at an alcohol concentration of 3.3 g/100 g ethanol, the beer would contain 92.5 cal/12 oz. The carbohydrate composition shown in Table 7 shows that the nonfermentable fraction was nearly equal to that of Beer #2.

EXAMPLE 11

Superattenuation of fermenting beer with rice pullulanase-malt beta-amylase

The wort was aerated and pitched as described in Example 8. Rice pullulanase (15.3 U/l) and malt beta-amylase (140 U/l) were added as described in Table 5 and the beer fermented at 15° C. in the normal manner.

The results in Table 6 indicate that this beer (#6) end-fermented in 8 days, which was faster than the glucoamylase control (Beer #2) or any of the beers formulated with rice pullulanase in conjunction with the other grain diastases. Again, the carbohydrate composition was similar to that of the glucoamylase control as shown in Table 7. A beta-amylase such as that obtained by the process of Example 7(B) or that obtained from ungerminated barley is superior and is preferred to any of the diastases (containing both alpha- and beta-amylase) used in the previous examples. (See beer 6 of Table 6 and beer 19 of Table 15).

EXAMPLE 12

Superattenuation of fermenting beer with rice and malt flours

Polished #4 brewer's rice and high gib distiller's malt were ground to 20 mesh in a Wiley mill. They were added to the wort aerated, and pitched as described above. One wort (Beer #7, Table 6) contained 5.2 g rice flour and 0.12 g malt flour/liter, while the other (Beer #8) contained twice as much of each flour. The worts were fermented as described above. The grain additions to Beer #7 were calculated to yield 15.4 units pullulanase per liter and 140 units of malt diastase per liter based on extraction as illustrated in Examples 3 and 7(A), respectively.

The data obtained for Beers #7 and #8 in Table 6 shows that both beers attenuated to the same level as the glucoamylase control (Beer #2) and the beers illustrated in Examples 8-11 in which enzyme extracts were employed.

EXAMPLE 13

Rice pullulanase used with glucoamylase to shorten fermentation time

The wort was used to set up 5 separate fermentations. All the worts were aerated and pitched after which glucoamylase (2.0 U/l; 4.0 U/l or 8.1 U/l) and rice pullulanase (3.8 U/l or 15.3 U/l) were added as described in Table 8. From the results in Table 9, it can readily be seen that the addition of rice pullulanase significantly shortened the fermentation time over the glucoamylase control even at reduced glucoamylase (Beers #11 and 12) or pullulanase concentration (Beer #13).

EXAMPLE 14

Use of malted rice extract to superattenuate beer

When pullulanase extracted from polished rice is used to superattenuate beer, it is necessary to add a separate alpha 1,4 glycosidase (e.g. the grain diastases described in Examples 7(A)-(E) above) to hydrolyze the alpha 1,4 dextrins, formed by the debranching action of pullulanase, to fermentable sugars (DP-1-DP-3). As is evident from Table 13, germination of whole rice results in a 16 fold increase in amylase (alpha 1,4 glycosidase) activity. Thus it was felt that malted rice extract alone could be used to superattenuate beer.

Table 14 lists the enzyme addition rates to beers #19 and 20. Beer #19 was superattenuated with polished rice pullulanase (alpha 1,6 glycosidase) together with barley diastase (the alpha, 1,4 glycosidase), while beer #20 was superattenuated with a malted rice extract similar to that cited in Example 4 which contains both alpha 1,6 and alpha 1,4 glycosidase activities. In both cases the pullulanase activity was adjusted to 15 U/l and in the case of beer #20 (malted rice) the amylase activity was 133 U/l at that pullulanase level. Beer #19 received 140 U/l barley diastase, since the polished rice pullulanase preparation contributed only 8 U/l.

Table 15 shows that both beers superattenuated to the same level as beers #2-8 (Table 6) in 8 days. HPLC analyses revealed that the carbohydrate composition of beers #19 and 20 were identical to each other and beers 2-8.

The germination of rice results in the synthesis of high levels of alpha and beta amylases while the pullulanase level remains constant. Thus pullulanase extracted from malted rice contains sufficient alpha 1,4 glycosidase activity so that beer may be superattenuated with this enzyme preparation alone (beer #20). In contrast, the amylase level of ungerminated rice is very low (Table 13) and it is necessary to supplement the alpha 1,4 glycosidase activity with an extract of barley (beer #19) or any of the diastases cited in Examples 8-11.

EXAMPLE 15

Conversion of all-malt wort prior to fermentation with rice pullulanase-malt beta-amylase An all-malt wort was obtained following kettle-boil. Three wort samples were converted with malt beta-amylase (1450 U/l) in conjunction with decreasing concentrations of rice pullulanase (150 U/l; 75 U/l and 38 U/l). Another sample of the wort was converted using rice pullulanase in conjunction with glucoamylase.

In all cases the procedure was the same. The worts were equilibrated at 60° C. with stirring in a water bath. The enzyme concentrations were adjusted to the levels shown in Table 10A. Incubation was allowed to continue for 30 minutes after which they were delivered into a flask contained in a vigorously boiling water bath. They were allowed to remain there for 2 hr to inactivate the enzymes. The worts were then cooled, and the resulting trub was removed by centrifugation.

The malt to syrup adjunct ratio was adjusted to the same level as the wort described in Examples 8-14. The worts were then pitched, aerated, and fermented as described in Example 8.

The beers were superattenuated relative to the no-enzyme control (Beer #1, Table 6). When packaged at 3.3 g/100 g ethanol, the caloric content of these beers would be about 98 calories, some 10 calories less than Beer 190 1 formulated with no enzyme addition. The carbohydrate compositions of the end fermented beers are given in Table 12.

EXAMPLE 16

Addition of grain amylases to preconverted beers

Since the beers cited in Example 15 did not superattenuate to the same level as the beers cited in Examples 8-14, various enzymes were added to see if the attenuation limit could be decreased. The yeast was removed from Beer #14 by centrifugation, and the clarified beer was split into two equal portions designated 14A and 14B. Both beers were repitched and received the enzymes listed in Table 10B. To Beer #14A was added 140 U/l of malt betaamylase and to Beer #14B was added 15.3 U/l of the rice pullulanase and 140 U/l of malt beta-amylase. Fermentation was then continued at 15° C.

Beers #15A and #16A were not repitched. Instead, the enzymes were injected directly into the fermenting beers according to the schedule listed in Table 10B.

The results of the secondary fermentation are listed in Table 11. The addition of the alpha 1,4 carbohydrase, malt beta-amylase, did not significantly reduce the specific gravity (Beer #14A), suggesting that most of the nonfermentable sugars contained alpha 1,6 linkages. In contrast, malt beta-amylase in conjunction with rice pullulanase (Beers #14B and #16A), or rice pullulanase alone (Beer #15A), superattenuated the beers to the same level as the glucoamylase control (Beer #2) or the beers described in Examples 8-14.

EXAMPLE 17

Addition of rice pullulanase at mash-in

Rice pullulanase, prepared as described in Example 3, was added to 400 ml foundation water to a final concentration of 520 U/l at 46° C. Then, 129.6 g pale malt were doughed in, and the mash was subjected to the following mash cycle: (1) 46° C. for 30 min; and (2) 60° C. for 120 min. The brew was mashed-off at 77° C. after which the spent grain was removed by filtration through cheesecloth. The first wort was clarified by centrifugation, diluted, and placed in a boiling water bath for 2 hr. All subsequent steps were as described in Example 15.

This beer end-fermented to a final specific gravity of 1.0019 (0.49° P) as opposed to 1.0029 (0.75° P) for Beer #1, the no enzyme control cited in Example 8. Thus, incorporation of rice pullulanase in the mash reduced the attenuation limit by 0.26° P. The carbohydrate composition of this beer (#18) is given in Table 12.

TABLE 1

EXTRACTION FROM WHOLE RICE
pH 6.0 - 50° C. Extraction

| Step | Total Volume (ml) | Protein mg/ml | Protein Total, mg | Specific Activity U/mg | Total Pullulanase Activity | Purification[1] | % Yield[1] |
|---|---|---|---|---|---|---|---|
| (1) Extract | 1310 | 2.48 | 3250 | $2.2 \times 10^{-1}$ | 715 | — | 100 |
| (2) pH Adjusted Supernatant | 1315 | 1.99 | 2617 | $2.2 \times 10^{-1}$ | 576 | 1.0 | 81 |
| (3) $(NH_4)_2SO_4$—Precipitate | 387 | 1.97 | 763 | $4.5 \times 10^{-1}$ | 344 | 2.0 | 48 |

[1]Overall

TABLE 2

EXTRACTION OF PEARLED RICE FRACTIONS

| Fraction | Weight (g) | Total Volume (ml) | Protein mg/ml | Protein Total, mg | Protein mg/g | Specific Activity U/mg | Total Pullulanase Activity |
|---|---|---|---|---|---|---|---|
| Whole rice | 100 | 300 | 2.78 | 834 | 8.34 | $2.68 \times 10^{-1}$ | 224 |
| Brown rice | 100 | 275 | 2.28 | 627 | 6.27 | $4.77 \times 10^{-1}$ | 301 |
| Polished rice | 100 | 260 | 1.19 | 309 | 3.09 | 1.06 | 328 |
| Husk | 25 | 325 | 0.24 | 78 | 3.12 | $6.0 \times 10^{-2}$ | 4.7 |
| Bran | 50 | 275 | 6.21 | 1708 | 34.2 | $3.2 \times 10^{-2}$ | 51.2 |

TABLE 3

ISOLATION OF PULLULANASE FROM POLISHED RICE

| Step | Description | Total Volume (ml) | Protein mg/ml | Protein Total, mg | Specific Activity U/mg | Total Activity | % Yield Step | % Yield Overall | Fold Purification Step | Fold Purification Overall |
|---|---|---|---|---|---|---|---|---|---|---|
| 1 | Extract | 2460 | 2.08 | 5117 | 1.15 | 5884 | — | 100 | — | — |
| 2 | pH Adjust | 2491 | 1.16 | 5081 | 1.20 | 6097 | 100 | 100 | 1.04 | 1.04 |
| 3 | $NH_4HCO_3$ diafiltrate | 628 | 4.85 | 3044 | 1.99 | 6057 | 99 | 100 | 1.66 | 1.73 |
| 4 | Freeze dried powder | — | — | — | 1.61 | — | — | 81 | 0.81 | 1.40 |

TABLE 4

AMYLASE ACTIVITIES OF GRAIN AMYLASES

| Amylase | Specific Activity U/mg Protein |
|---|---|
| Malt diastase | 81.1 |
| Malt beta-amylase | 13.9 |
| Soybean diastase | 9.0 |
| Wheat diastase | 31.5 |
| Barley diastase | 23.0 |

TABLE 5

ENZYME ADDITIONS TO FERMENTING BEERS

| Beer # | Example # | Gluco-amylase | Rice Pullula-nase | 1,4 Carbohydrase |
|---|---|---|---|---|
| 1 | 8–12 | 0 | 0 | 0 |
| 2 | 8–12 | 8.1 | 0 | 0 |
| 3 | 8 | 0 | 15.3 | 140 (malt diastase) |
| 4 | 9 | 0 | 15.3 | 140 (soybean diastase) |
| 5 | 10 | 0 | 15.3 | 140 (wheat diastase) |
| 6 | 11 | 0 | 15.3 | 140 (malt beta-amylase) |

TABLE 6

REAL EXTRACT, AND CALORIC CONTENT OF SUPERATTENUATED BEERS

| Beer # | Example # | Enzymes Used to Superattenuate | Days Fermented | Specific Gravity at End Fermentation | Real Extract g/100 ml at 3.3% Alcohol | Calories/12 oz at 3.3% w/v Alcohol |
|---|---|---|---|---|---|---|
| 1 | 8–12 | None | 13 | 1.0029 | 1.99 | 108.3 |
| 2 | 8–12 | Glucoamylase | 15 | 0.9965 | 0.99 | 92.5 |
| 3 | 8 | Malt diastase + rice pullulanase | 15 | 0.9969 | 1.02 | 92.9 |
| 4 | 9 | Soybean diastase + rice pullulanase | 17 | 0.9969 | 1.05 | 93.4 |
| 5 | 10 | Wheat diastase + rice pullulanase | 15 | 0.9967 | 0.99 | 92.5 |
| 6 | 11 | Malt beta-amylase + rice pullulanase | 8 | 0.9966 | 0.99 | 92.7 |
| 7 | 12 | Malt and rice flour | 11 | 0.9964 | 0.98 | 92.4 |
| 8 | 12 | Malt and rice flour | 8 | 0.9966 | 1.01 | 92.8 |

TABLE 7

CARBOHYDRATE COMPOSITION OF SUPER-ATTENUATED BEERS AT END-FERMENTATION

| Beer # | Example # | Sugar g/100 ml[1] | | | | |
|---|---|---|---|---|---|---|
| | | Total | DP-1 | DP-2 | DP-3 | >DP-3 |
| 1 | 8-12 | 2.40 | 0.01 | 0.13 | Trace | 2.26 |
| 2 | 8-12 | 0.83 | 0.05 | 0.13 | 0.14 | 0.51 |
| 3 | 8 | 0.91 | 0.05 | 0.16 | 0.17 | 0.53 |
| 4 | 9 | 1.11 | 0.17 | 0.25 | 0.24 | 0.45 |
| 5 | 10 | 1.04 | 0.10 | 0.22 | 0.18 | 0.54 |
| 6 | 11 | 0.78 | 0.05 | 0.16 | 0.17 | 0.41 |

All sugars are identified by degree of polymerization [DP number]; e.g.
DP-1 = monosaccharide assumed to be predominantly glucose
DP-2 = disaccharide assumed to be predominantly maltose
DP-3 = trisaccharide assumed to be predominantly maltotriose
>DP-3 = higher saccharides which are nonfermentable

TABLE 8

RICE PULLULANASE AND GLUCOAMYLASE ADDITIONS TO SUPERATTENUATING BEERS

| Beer # | Enzyme Concentration U/l | |
|---|---|---|
| | Glucoamylase | Rice Pullulanase |
| 9 | 8.1 | 0 |
| 10 | 8.1 | 15.3 |
| 11 | 4.0 | 15.3 |
| 12 | 2.0 | 15.3 |
| 13 | 8.1 | 3.8 |

TABLE 9

REAL EXTRACT AND CALORIE CONTENT OF BEERS SUPERATTENUATED WITH RICE PULLULANASE-GLUCOAMYLASE

| Beer # | Days Fermented | Specific Gravity | Real Extract g/100 at 3.3% Alcohol | Calories/12 oz. at 3.3 g/100 Ethanol |
|---|---|---|---|---|
| 9 | 12 | .9966 | 1.01 | 92.8 |
| 10 | 7 | .9966 | 1.00 | 92.6 |
| 11 | 8 | .9967 | 1.02 | 92.9 |
| 12 | 11 | .9966 | 1.01 | 92.8 |
| 13 | 11 | .9965 | 0.97 | 92.2 |

TABLE 10A

ENZYME ADDITIONS TO ALL-MALT WORT PRIOR TO FERMENTATION

| Beer # | Enzyme Concentration U/l Wort | | |
|---|---|---|---|
| | Rice Pullulanase | Malt beta-Amylase | Glucoamylase |
| 14 | 150 | 1450 | — |
| 15 | 75 | 1450 | — |
| 16 | 38 | 1450 | — |
| 17 | 150 | — | 80 |

TABLE 10B

ENZYME ADDITION TO PRECONVERTED BEERS IN FERMENTATION

| Beer # | Parent Beer | Enzyme Concentration U/l | |
|---|---|---|---|
| | | Rice Pullulanase | Malt beta-Amylase |
| 14-A | 14 | — | 140 |
| 14-B | 14 | 15.3 | 140 |
| 15-A | 15 | 15.3 | — |
| 16-A | 16 | 15.3 | 140 |

TABLE 11

REAL EXTRACT AND CALORIE CONTENT OF BEERS CONVERTED PRIOR TO FERMENTATION

| Beer # | Days Fermented | Specific Gravity | Real Extract g/100 at 3.3% Ethanol | Calories/12 oz. at 3.3 g/100 Ethanol |
|---|---|---|---|---|
| 14 | 11 | .9989 | 1.36 | 97.9 |
| 15 | 9 | .9986 | 1.36 | 97.3 |
| 16 | 8 | .9991 | 1.38 | 98.4 |
| 17 | 8 | .9987 | 1.32 | 97.4 |
| 14A | 10[1] | .9983 | — | — |
| 14B | 5[1] | .9964 | 0.97 | 92.1 |
| 15A | 6[1] | .9966 | 1.01 | 92.9 |
| 16A | 4[1] | .9966 | 1.00 | 92.6 |

[1]Days fermentation following enzyme addition to fermenting beers.

TABLE 12

CARBOHYDRATE COMPOSITION OF PRECONVERTED BEERS NEAR END-FERMENTATION FROM EXAMPLES 15 AND 17

| Beer # | Days Fermented | Sugar g/100 ml | | | | |
|---|---|---|---|---|---|---|
| | | Total | DP-1 | DP-2 | DP-3 | >DP-3 |
| 14 | 11 | 1.74 | .08 | .26 | .46 | 0.94 |
| 15 | 9 | 1.59 | .10 | .21 | .43 | 0.85 |
| 16 | 8 | 1.64 | .07 | .22 | .40 | 0.95 |
| 17 | 7 | 1.38 | .03 | .22 | .38 | 0.75 |
| 18 | | 2.40 | — | .41 | .68 | 1.31 |

TABLE 13

Pullulanase and Amylase Activities in Rice Extracts

| Type of Rice | Total Protein mg. | Pullulanase | | Amylase | |
|---|---|---|---|---|---|
| | | Specific Activity | Total Activity | Specific Activity | Total Activity |
| Polished | 336 | 0.76 | 254 | 0.34 | 113 |
| Malted | 653 | 0.38 | 248 | 2.74 | 1789 |

TABLE 14

Enzyme Addition Rate to Fermenting Beers

| Beer # | Enzymes Used For Super-attenuation | Pulluanase Addition Rate u/l | Amylase Addition Rate u/l From | | |
|---|---|---|---|---|---|
| | | | Rice | Barley | Malted Rice |
| 19 | Polished Rice Pullulanase and Barley Diastase | 15 | 8 | 140 | — |
| 20 | Malted Rice Extract | 15 | — | — | 133 |

TABLE 15

Real Extract and Calorie Content of Superattenuated Beers

| Beer # | Enzymes Used To Super-attenuate | Days Fermented | Specific Gravities At End Fermentation | Real Extract g/100 ml at 3.3% Alcohol | Calories/ 12 oz. at 3.3% w/v Alcohol |
|---|---|---|---|---|---|
| 19 | Polished Rice Pullulanase and Barley Diastase | 8 | 0.9966 | 1.00 | 92.7 |
| 20 | Malted Rice Extract | 8 | 0.9964 | 0.97 | 92.2 |

The rice which may be used as the source of the enzyme of the present invention is food-grade rice which has been treated at conditions mild enough to preserve the enzymatic activity. If ungerminated rice is used, either seed or polished dry milled rice may be used. However, the preferred source is commercially polished dry milled brewer's rice for the reasons outlined above [i.e., ease of procurement, higher specific activity yield, economy]. We have shown that the enzyme may be extracted from a wide variety of seed grade rice including LaBelle, Lebonnet, Nato, Sterbonnet, or Brazos. Thus any of these varieties would suffice if the rice is malted prior to extraction to order to increase amylase activity. LaBelle was chosen for these studies since it is the most plentiful domestic variety.

If the enzyme is extracted from rice prior to use in this process, the spent rice from which the enzyme has been extracted can be utilized as a starch source in mashing or for adjunct syrup formulation to make the use of the rice enzyme more economical.

Although the use of the rice debranching enzyme which has been described in its use in preparing a low calorie or superattenuated beer, it might possibly have other applications. For example, a mixture of the rice debranching enzyme and a grain diastase may be advantageously used to prepare a starch conversion product having a high maltose content such as that described in U.S. Patent No. 3,996,107. Because of its natural origin, the debranching enzyme from rice would no doubt be approved for use in food products without too much difficulty.

It will be apparent to those skilled in the art that a number of modifications and changes can be made without departing from the spirit and scope of the present invention. Therefore, it is intended that the scope of the invention be limited only by the claims which follow.

REFERENCES

1. Miller, G. Anal. Chem. 31, 964, 1959.
2. Bernfield, P. Advances in Enzymology XII (Nord, F., ed.) 379, Intersciences Publishers, New York, 1951.
3. Pazur, J. Methods in Enzymology XXVIII, Ginsberg, V. (ed.) 931, Academic Press, 1975.
4. Kneen, E. (ed.). "Alcohol Determined Refractometrically" in *Methods of Analysis of the American Society of Brewing Chemists,* 7th Revised edition, published by the Society, 1976.
5. Olshausen, J. Brewers Digest 27, 45, 1952.
6. Olshausen, J. Brewers Digest 27, 53, 1952.
7. Helbert, J. R. J. Amer. Soc. Brew. Chem. 36, 66, 1978.
8. Martinelli, L. (Chairman) ASBC Journal 35, p. 104, 1978.
9. Scobell, H., Brobst, K. and Steele, F. Cereal Chem. 54, p. 905, 1975.
10. Greenwood, C. and A. MacGregor. J. Inst. Brew. 71, 408, 1965.

We claim:

1. The method of extracting a debranching enzyme of high specific activity from rice which comprises selecting as the starting material a member selected from the class consisting of polished rice and malted rice, slurrying the rice in a 0.1 M potassium phosphate-0.2 M sodium chloride buffer system having a pH of 6 at a temperature of about 50° C. for about 3 hours to obtain an extract containing the debranching enzyme, clarifying the extract by centrifugation and retaining the supernatant which contains the enzyme.

2. The method of claim 1 in which the supernatant containing the enzyme is dialyzed against a solution of a salt which sublimes on freeze drying and freeze dried to yield a salt-free enzyme powder which is storage stable.

3. The method of extracting an enzyme mixture useful in the preparation of malt beverages from rice, which mixture includes a debranching enzyme of high specific activity and a diastase, said method comprising selecting as the starting material malted rice, preparing a defatted flour from said rice, suspending said defatted malted rice flour in an 0.1 M potassium phosphate-0.2 M sodium chloride extraction buffer having a pH of about 6 at a temperature of about 50° C. for about 3 hours to obtain an extract containing the mixture of enzymes, clarifying the extract by centrifugation and retaining the supernatant which contains the enzyme mixture.

* * * * *